(12) United States Patent
Lynn et al.

(10) Patent No.: US 7,780,994 B2
(45) Date of Patent: Aug. 24, 2010

(54) COMPOSITE BIOMATERIALS COMPRISING CALCIUM PHOSPATE MATERIALS, COLLAGEN AND GLYCOSAMINOGLYCANS

(75) Inventors: Andrew Lynn, Cambridge (GB); Ruth Cameron, Cambridge (GB); Serena Best, Cambridge (GB); William Bonfield, Cambridge (GB)

(73) Assignee: Cambridge Enterprise Limited, Cambridge (GB)

( * ) Notice: Subject to any disclaimer, the term of this patent is extended or adjusted under 35 U.S.C. 154(b) by 877 days.

(21) Appl. No.: 10/595,587

(22) PCT Filed: Oct. 28, 2004

(86) PCT No.: PCT/GB2004/004550

§ 371 (c)(1),
(2), (4) Date: Jan. 4, 2007

(87) PCT Pub. No.: WO2005/051447

PCT Pub. Date: Jun. 9, 2005

(65) Prior Publication Data

US 2007/0134285 A1 Jun. 14, 2007

(30) Foreign Application Priority Data

Oct. 28, 2003 (GB) .................. 0325161.8

(51) Int. Cl.
*A61K 33/42* (2006.01)
*A61K 6/00* (2006.01)
(52) U.S. Cl. .............. 424/602; 424/601; 424/603; 424/423; 424/401; 514/2
(58) Field of Classification Search ........... None
See application file for complete search history.

(56) References Cited

U.S. PATENT DOCUMENTS

| 5,071,436 A | 12/1991 | Huc et al. |
|---|---|---|
| 5,320,844 A | 6/1994 | Liu |
| 5,739,286 A | 4/1998 | Silver et al. |
| 6,432,710 B1 | 8/2002 | Boss, Jr. et al. |
| 6,733,582 B1 * | 5/2004 | Bohner et al. ............ 106/690 |

FOREIGN PATENT DOCUMENTS

| EP | 0383568 A2 | 8/1990 |
|---|---|---|
| EP | 0842670 A1 | 5/1998 |
| JP | 63229058 | 9/1988 |
| WO | 0016822 A1 | 3/2000 |

OTHER PUBLICATIONS

Serre et al., "Influence of magnesium substitution on a collagen-apatite biomaterial on the production of a calcifying matrix by human osteoblasts", Journal of Biomedical Materials Research, Dec. 15, 1998, pp. 626-633, vol. 42, No. 4.
Hemmerle et al., "Long-term behaviour of a hydroxyapatite/collagen-glycosaminoglycan biomaterial used for oral surgery: a case report", Journal of Materials Science: Materials in Medicine, Jun. 1995, pp. 360-366, vol. 6, No. 6.
Bakos et al., "Hydroxyapatite-collagen-hyaluronic acid composite", Biomaterials, Jan. 1999, pp. 191-195, vol. 20, No. 2, Elsevier Science Publishers.
Rovira et al; "Microstructural characterization of a calcium phosphate ESP-collagen composite", Seventh European Conference on Composite Materials. Realising Their Commercial Potential, London, UK, May 14-16, 1996, pp. 449-454, vol. 2.
Hemmerle et al., "Long-term behaviour of a hydroxyapatite/collagen-glycosaminoglycan biomaterial used for oral surgery: a case report", Journal of Materials Science: Materials in Medicine, vol. 6, No. 6, Jun. 1995, pp. 360-366.
Kikuchi et al., "Self-organization mechanism in a bone-like hydroxyapatite/collagen nanocomposite synthesized in vitro and its biological reaction in vivo", Biomaterials, vol. 22, Issue 13, Jul. 2001, pp. 1705-1711.

* cited by examiner

*Primary Examiner*—Hope A Robinson
(74) *Attorney, Agent, or Firm*—Senniger Powers LLP

(57) ABSTRACT

A process for the production of a composite material comprising collagen, brushite and one or more glycosaminoglycans, said process comprising the steps of providing an acidic aqueous solution comprising collagen, a calcium source and a phosphorous source and one or more glycosaminoglycans, and precipitating the collagen, the brushite and the one or more glycosaminoglycans together from the aqueous solution to form a triple co-precipitate.

31 Claims, 12 Drawing Sheets

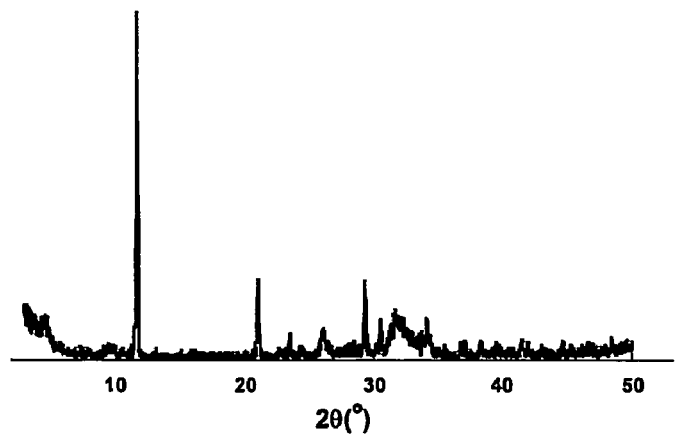
Figure 1: XRD pattern of composite following co-precipitation (Cu-Kα radiation).
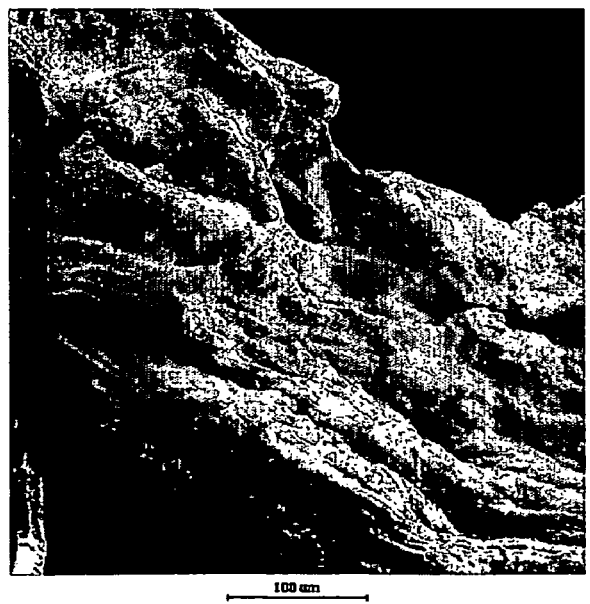
Figure 2: SEM micrograph of triple co-precipitate.

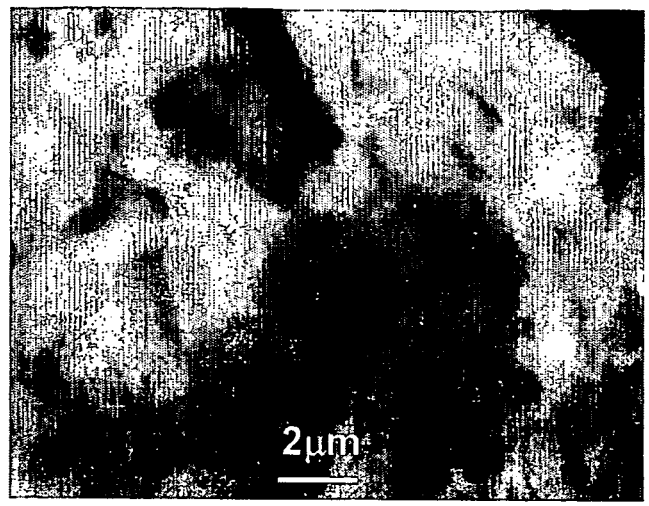
Figure 3: TEM micrograph of triple co-precipitate
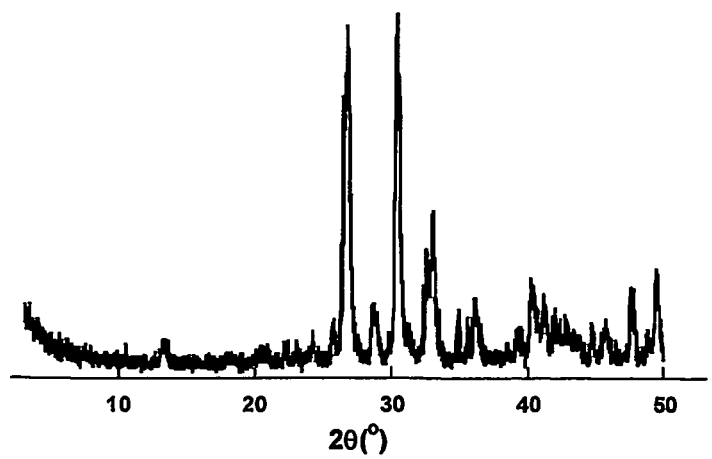
Figure 4: XRD pattern of composite following dehydrothermal treatment at 105°C and 50mTorr for 48 hours, indicating that the brushite phase has converted to its dehydrated form monetite.

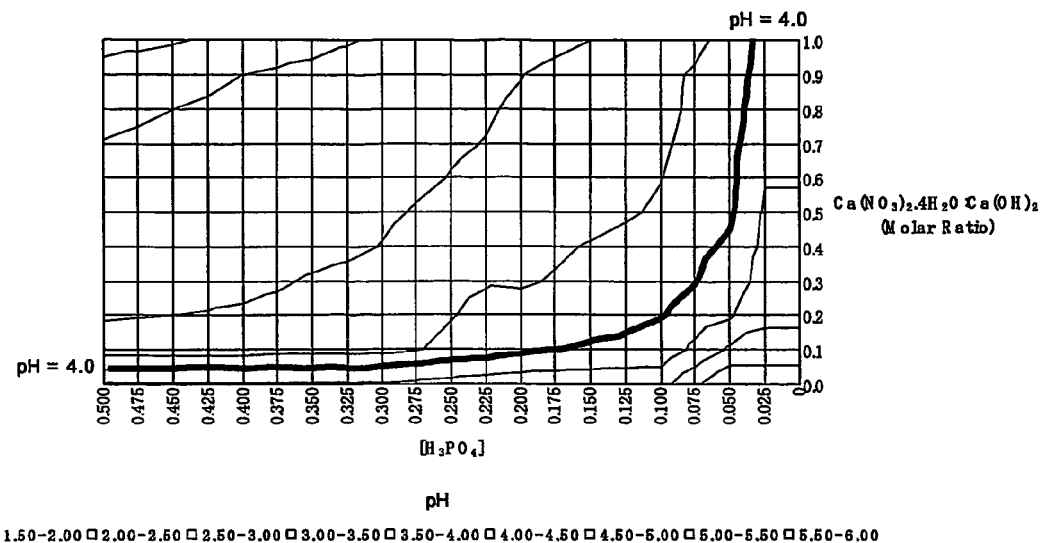
□ 1.50-2.00 □ 2.00-2.50 □ 2.50-3.00 □ 3.00-3.50 □ 3.50-4.00 □ 4.00-4.50 □ 4.50-5.00 □ 5.00-5.50 □ 5.50-6.00
Figure 5: set of combinations of ionic concentration and calcium nitrate: calcium hydroxide ratio for maintaining pH = 4.0.
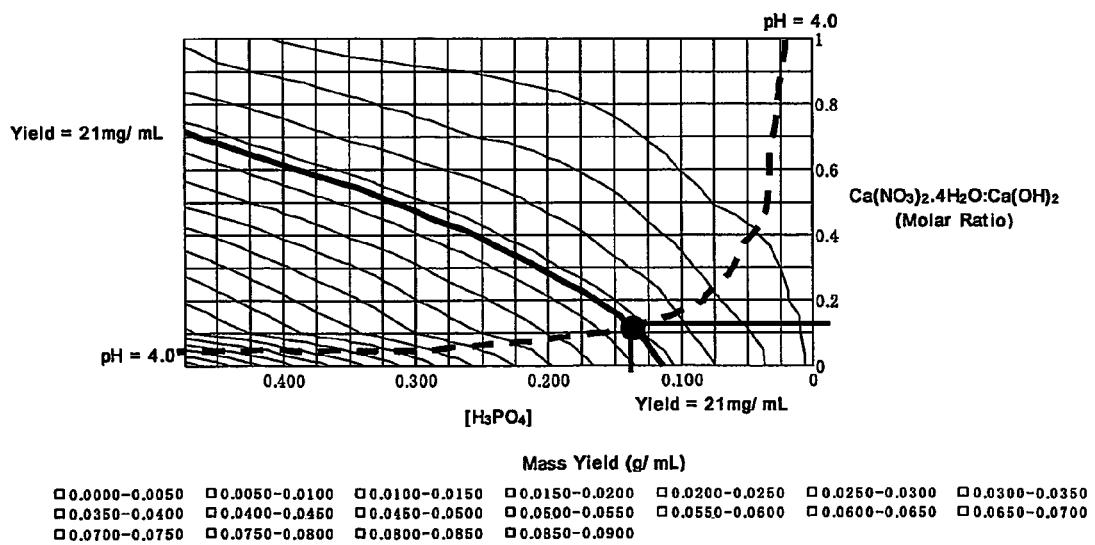
Mass Yield (g/mL)
□ 0.0000-0.0050 □ 0.0050-0.0100 □ 0.0100-0.0150 □ 0.0150-0.0200 □ 0.0200-0.0250 □ 0.0250-0.0300 □ 0.0300-0.0350
□ 0.0350-0.0400 □ 0.0400-0.0450 □ 0.0450-0.0500 □ 0.0500-0.0550 □ 0.0550-0.0600 □ 0.0600-0.0650 □ 0.0650-0.0700
□ 0.0700-0.0750 □ 0.0750-0.0800 □ 0.0800-0.0850 □ 0.0850-0.0900
Figure 6: Identification of conditions for pH 4.0 synthesis of a triple coprecipitate slurry containing a 1:1 mass ratio of calcium phosphate to collagen plus GAG.

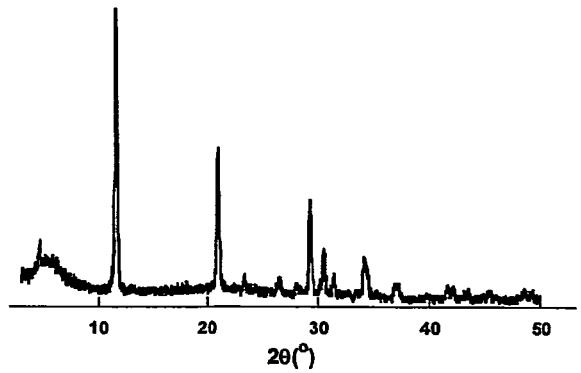
Figure 7: x-ray diffraction pattern of collagen/GAG/brushite triple coprecipitate following removal of unbound water (Cu-K$_\alpha$ radiation).
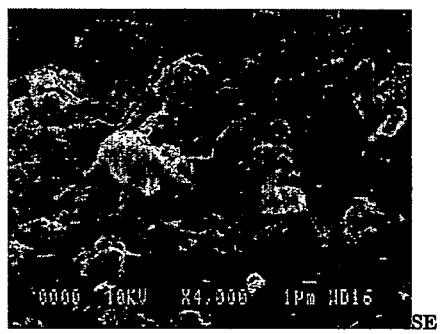
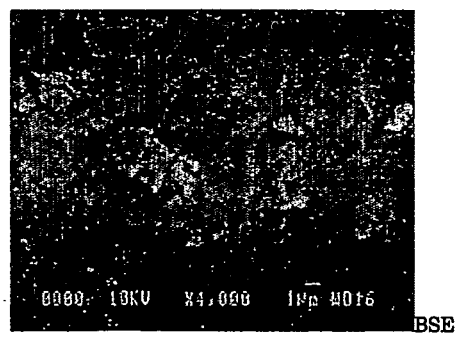
Figure 8: Secondary (SE) and backscattered electron (BSE) images of surface of triple coprecipitate with CaP: collagen + GAG = 1:1.

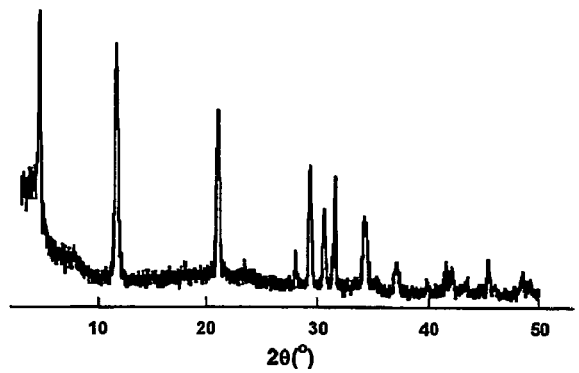

Figure 9: x-ray diffraction pattern of collagen/GAG/brushite triple coprecipitate following EDAC crosslinking (Cu-K$_\alpha$ radiation).

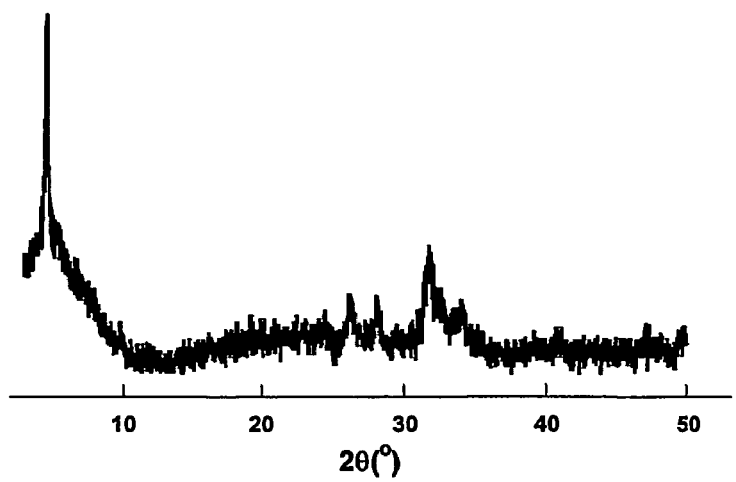

Figure 10: x-ray diffraction pattern of EDAC-crosslinked collagen/GAG/CaP triple coprecipitate following conversion at 37°C to octacalcium phosphate (OCP) over 72 hours at pH 6.67, to form a collagen/GAG/OCP biocomposite (Cu-K$_\alpha$ radiation).

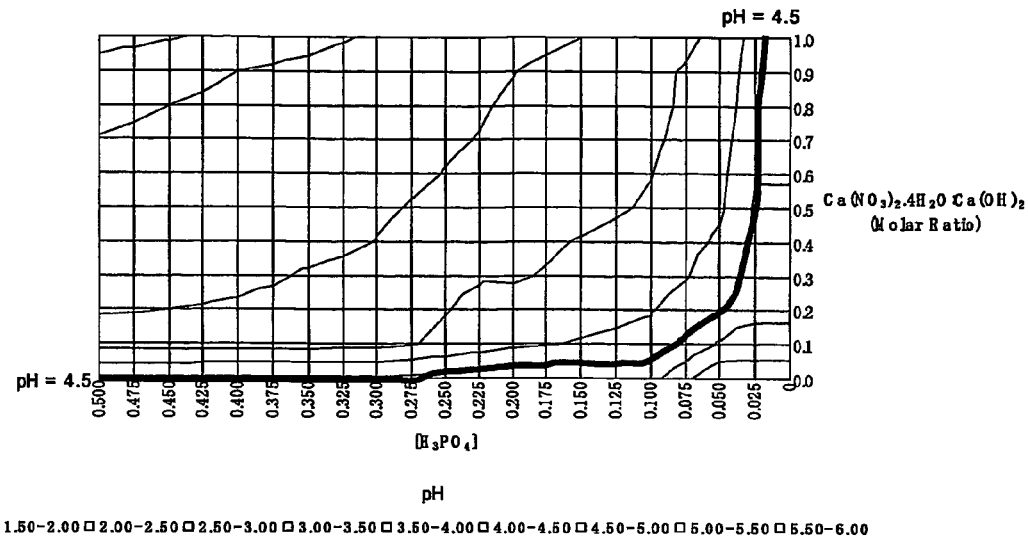
Figure 11: set of combinations of ionic concentration and calcium nitrate: calcium hydroxide ratio for maintaining pH = 4.5.
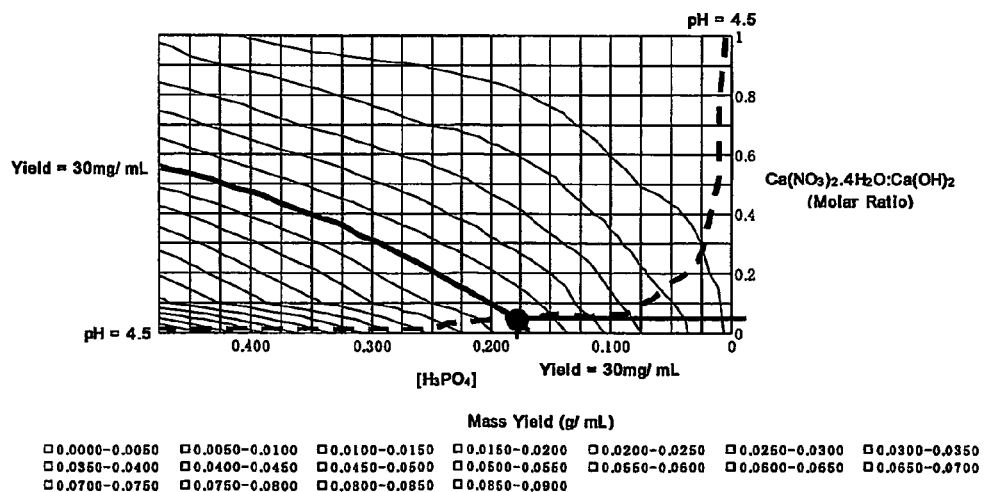
Figure 12: Identification of conditions for pH 4.5 synthesis of a triple coprecipitate slurry containing a 3:1 mass ratio of calcium phosphate to collagen plus GAG.

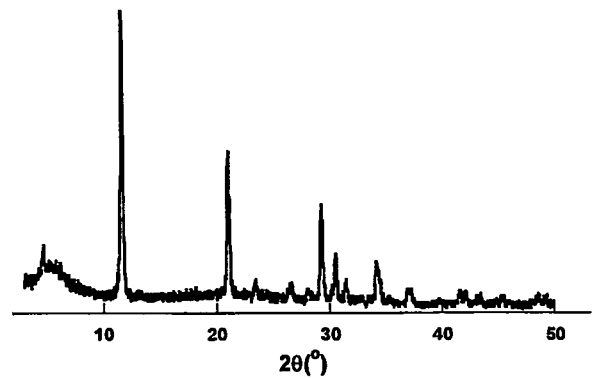
Figure 13: x-ray diffraction pattern of collagen/GAG/brushite triple coprecipitate following removal of unbound water (Cu-K$_\alpha$ radiation).
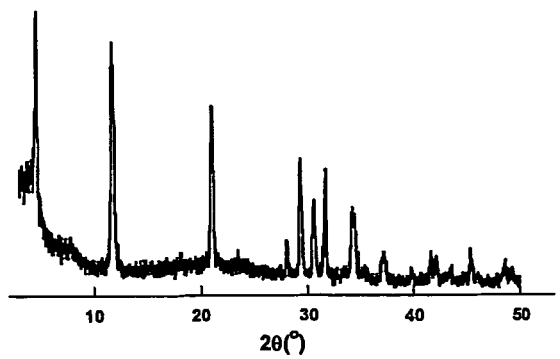
Figure 14: x-ray diffraction pattern of collagen/GAG/brushite triple coprecipitate following EDAC crosslinking (Cu-K$_\alpha$ radiation).

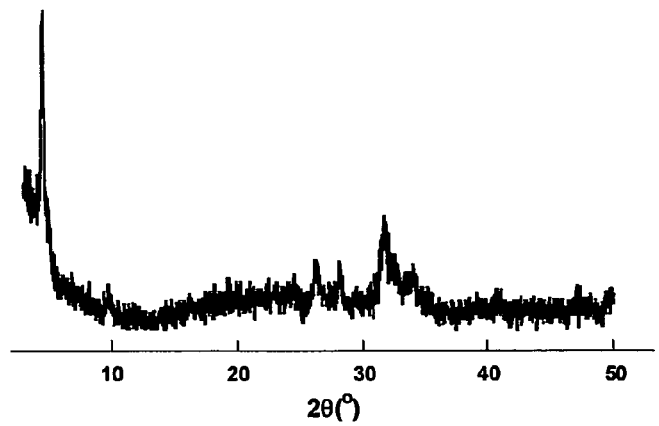

Figure 15: x-ray diffraction pattern of EDAC-crosslinked collagen/GAG/CaP triple coprecipitate following conversion at 37°C to apatite over 72 hours at pH 8.50, to form a collagen/GAG/apatite biocomposite (Cu-K$_\alpha$ radiation).

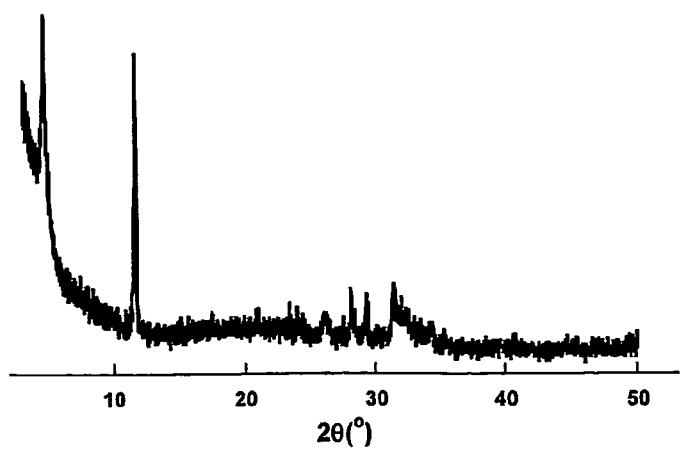

Figure 16: X-ray diffraction pattern of EDAC-crosslinked collagen/GAG/Ap triple coprecipitates after secondary crosslinking via gamma irradiation.

COMPOSITE BIOMATERIALS COMPRISING CALCIUM PHOSPATE MATERIALS, COLLAGEN AND GLYCOSAMINOGLYCANS

CROSS-REFERENCE TO RELATED APPLICATIONS

The present application is based on and claims the benefit of International (PCT) Application Serial No. PCT/GB2004/004550, filed on Oct. 28, 2004, which claims priority from GB Pat. No. 0325161.8, filed on Oct. 28, 2003. The entire contents of this application is incorporated herein by reference.

FIELD OF THE INVENTION

The present invention relates to the field of synthetic bone, dental materials and regeneration scaffolds for biomedical applications and, in particular, to synthetic bone, dental materials and regeneration scaffolds and their precursors comprising collagen, a calcium phosphate material and one or more glycosaminoglycans.

BACKGROUND OF THE INVENTION

Natural bone is a biocomposite of collagen, non-collagenous organic phases including glycosaminoglycans, and calcium phosphate. Its complex hierarchical structure leads to exceptional mechanical properties including high stiffness, strength, and fracture toughness, which in turn enable bones to withstand the physiological stresses to which they are subjected on a daily basis. The challenge faced by researchers in the field is to make a synthetic material that has a composition and structure that will allow natural bone growth in and around the synthetic material in the human or animal body.

It has been observed that bone will bond directly to calcium phosphates in the human body (a property referred to as bioactivity) through a bone-like apatite layer formed in the body environment. Collagen and copolymers comprising collagen and other bioorganics such as glycosaminoglycans on the other hand, are known to be optimal substrates for the attachment and proliferation of numerous cell types, including those responsible for the production and maintenance of bone in the human body.

Hydroxyapatite is the calcium phosphate most commonly used as constituent in bone substitute materials. It is, however, a relatively insoluble material when compared to other forms of calcium phosphate materials such as brushite, tricalcium phosphate and octacalcium phosphate. The relatively low solubility of apatite can be a disadvantage when producing a biomaterial as the rate of resorption of the material in the body is particularly slow.

Calcium phosphates such as hydroxyapatite are mechanically stiff materials. However, they are relatively brittle when compared to natural bone. Collagen is a mechanically tough material, but has relatively low stiffness when compared to natural bone. Materials comprising copolymers of collagen and glycosaminoglycans are both tougher and stiffer than collagen alone, but still have relatively low stiffness when compared to natural bone."

Previous attempts in the prior art of producing a synthetic bone-substitute material having improved mechanical toughness over hydroxyapatite and improved stiffness over collagen and copolymers of collagen and glycosaminoglycans include combining collagen and apatite by mechanical mixing. Such a mechanical method is described in EP-A-0164 484.

Later developments in the technology include producing a bone-replacement material comprising hydroxyapatite, collagen and chondroitin-4-sulphate by the mechanical mixing of these components. This is described in EP-A-0214070. This document further describes dehydrothermic crosslinking of the chondroitin-4-sulphate to the collagen. Materials comprising apatite, collagen and chondroitin-4-sulphate have been found to have good biocompatibility. The mechanical mixing of the apatite with the collagen, and optionally chondroitin-4-sulphate, essentially forms collagen/chondroitin-4-sulphate-coated particles of apatite. It has been found that such a material, although biocompatible, produces limited in-growth of natural bone when in the human or animal body and no remodeling of the calcium phosphate phase of the synthetic material.

SUMMARY OF THE INVENTION

The present invention seeks to address at least some of the problems associated with the prior art.

In a first aspect, the present invention provides a process for the production of a composite material comprising collagen, brushite and one or more glycosaminoglycans, said process comprising the steps of providing an acidic aqueous solution comprising collagen, a calcium source and a phosphorous source and one or more glycosaminoglycans, and precipitating the collagen, the brushite and the one or more glycosaminoglycans together from the aqueous solution to form a triple co-precipitate.

The term triple co-precipitate encompasses precipitation of the three compounds where the compounds have been precipitated at substantially the same time from the same solution/dispersion. It is to be distinguished from a material formed from the mechanical mixing of the components, particularly where these components have been precipitated separately, for instance in different solutions. The microstructure of a co-precipitate is substantially different from a material formed from the mechanical mixing of its components.

In the first aspect, the solution preferably has a pH of from 2.5 to 6.5, more preferably from 2.5 to 5.5. More preferably, the solution has a pH of from 3.0 to 4.5. Still more preferably, the solution has a pH of from 3.8 to 4.2. Most preferably, the solution has a pH of around 4.

BRIEF DESCRIPTION OF THE DRAWINGS

FIG. 1: XRD pattern of composite following co-precipitation (Cu-Kα radiation).

FIG. 2: SEM micrograph of triple co-precipitate.

FIG. 3: TEM micrograph of triple co-precipitate.

FIG. 4: XRD pattern of composite following dehydrothermal treatment at 150° C. and 50 mTorr for 48 hours, indicating that the brushite phase has converted to its dehydrated form monetite.

FIG. 5: set of combinations of ionic concentration and calcium nitrate: calcium hydroxide ratio for maintaining pH=4.0.

FIG. 6: Identification of conditions for pH 4.0 synthesis of a triple coprecipitate slurry containing a 1:1 mass ratio of calcium phosphate to collagen plus GAG.

FIG. 7: x-ray diffraction pattern of collagen/GAG/brushite triple coprecipitate following removal of unbound water (Cu-Kα radiation).

FIG. 8: Secondary (SE) and backscattered electron (BSE) images of surface of triple coprecipitate with CaP: collagen+ GAG=1:1.

FIG. 9: x-ray diffraction pattern of collagen/GAG/brushite triple coprecipitate following EDAC crosslinking (Cu-K$\alpha$ radiation).

FIG. 10: x-ray diffraction pattern of EDAC-crosslinked collagen/GAG/CaP triple coprecipitate following conversion at 37° C. to octacalcium phosphate (OCP) over 72 hours at pH 6.67, to form a collagen/GAG/OCP biocomposite (Cu-K$\alpha$ radiation).

FIG. 11: set of combinations of ionic concentration and calcium nitrate: calcium hydroxide ratio for maintaining pH=4.5.

FIG. 12: identification of conditions for pH 4.5 synthesis of a triple coprecipitate slurry containing a 3:1 mass ratio of calcium phosphate to collagen plus GAG.

FIG. 13: x-ray diffraction pattern of the collagen/GAG/ brushite triple coprecipitate following removal of unbound water (Cu-K$\alpha$ radiation).

FIG. 14: x-ray diffraction pattern of collagen/GAG/brushite triple coprecipitate following EDAC crosslinking (Cu-K$\alpha$ radiation).

FIG. 15: x-ray diffraction pattern of EDAC-crosslinked collagen/GAG/CaP triple coprecipitate following conversation at 37° C. to apatite over 72 hours at pH 8.50, to form a collagen/GAG/apatite biocomposite (Cu-K$\alpha$ radiation).

FIG. 16: x-ray diffraction pattern of EDAC-crosslinked collagen/GAG/Ap triple coprecipitates after secondary crosslinking via gamma irradiation.

DETAILED DESCRIPTION OF PREFERRED EMBODIMENTS

Figure 17:
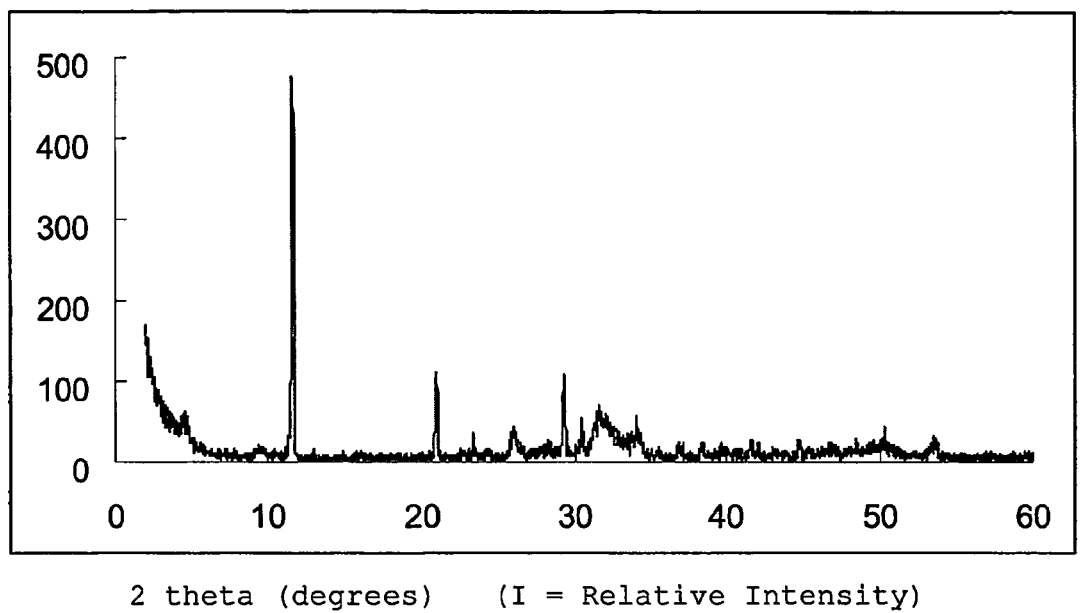
FIG. 17: XRD pattern of composite following triple coprecipitation and drying of Example 4.

The calcium source is preferably selected from one or more of calcium nitrate, calcium acetate, calcium chloride, calcium carbonate, calcium alkoxide, calcium hydroxide, calcium silicate, calcium sulphate, calcium gluconate and the calcium salt of heparin. A calcium salt of heparin may be derived from the porcine intestinal mucosa. Suitable calcium salts are commercially available from Sigma-Aldrich Inc.

The phosphorus source is preferably selected from one or more of ammonium-dihydrogen phosphate, diammonium hydrogen phosphate, phosphoric acid, disodium hydrogen orthophosphate 2-hydrate ($Na_2HPO_4 \cdot 2H_2O$, sometimes termed GPR Sorensen's salt) and trimethyl phosphate, alkali metal salts (e.g Na or K) of phosphate, alkaline earth salts (e.g. Mg or Ca) of phosphate.

Glycosaminoglycans are a family of macromolecules containing long unbranched polysaccharides containing a repeating disaccharide unit. Preferably, the one or more glycosaminoglycans are selected from chondroitin sulphate, dermatin sulphate, heparin, heparin sulphate, keratin sulphate and hyaluronic acid. Chondroitin sulphate may be chondroitin-4-sulphate or chondroitin-6-sulphate, both of which are available from Sigma-Aldrich Inc. The chondroitin-6-sulphate may be derived from shark cartilage. Hyaluronic acid may be derived from human umbilical chord. Heparin may be derived from porcine intestinal mucosa.

Preferably, in the precipitation of the triple co-precipitate, the solution has a temperature of from 4.0 to 50° C. More preferably, the solution has a temperature of from 15 to 40° C. The solution may be at room temperature, that is from 20 to 30° C., with a temperature of from 20 to 27° C. being preferred. Most preferably, the temperature is around 25° C.

The concentration of calcium ions in the aqueous solution is typically from 0.00025 to 1 moldm$^{-3}$ and preferably from 0.001 to 1 moldm$^{-3}$. Where the process includes the additional further steps of filtration and/or low temperature drying, the concentration of calcium ions in the aqueous solution is more preferably from 0.05 to 0.5 moldm$^{-3}$ (for example from 0.08 to 0.25 moldm$^{-3}$) and most preferably from 0.1 to 0.5 moldm$^{-3}$. Where the process includes the additional further steps of freeze drying and optionally injection moulding, the concentration of calcium ions in the aqueous solution is more preferably from 0.01 to 0.3 moldm$^{-3}$ and most preferably from 0.05 to 0.18 moldm$^{-3}$.

Preferably, the solution comprises phosphate ions and the concentration of phosphate ions in solution is typically from 0.00025 to 1 moldm$^{-3}$ and preferably from 0.001 to 1 M. Where the process includes the additional further steps of filtration and/or low temperature drying, the concentration of phosphate ions in solution is more preferably 0.05 to 0.5 moldm$^{-3}$, still more preferably 0.1 to 0.5 M, for example 0.1 to 0.35 moldm$^{-3}$. Where the process includes the additional further steps of freeze drying and optionally injection moulding, the concentration of phosphate ions in solution is more preferably from 0.01 to 0.3 moldm$^{-3}$, still more preferably 0.05 to 0.18 M.

Preferably, the ratio of collagen to the total amount of one or more glycosaminoglycans in the solution prior to precipitation is from 8:1 to 30:1 by weight. More preferably, the ratio of collagen to the total amount of one or more glycosaminoglycans is from 10:1 to 12:1, and most preferably the ratio is from 11:1 to 23:2.

Preferably, the ratio of collagen to brushite in the triple co-precipitate is from 10:1 to 1:100 by weight, more preferably from 5:1 to 1:20, still more preferably from 3:2 to 1:10, most preferably from 3:2 to 1:4.

The concentration of collagen in the solution prior to precipitation is typically from 1 to 20 g/L, more preferably from 1 to 10 g/L. Where the process includes the steps of filtration and/or low temperature drying, the concentration of collagen in the solution is more preferably from 1 to 10 g/L, still more preferably from 1.5 to 2.5 g/L, and most preferably 1.5 to 2.0 g/L. Where the process includes freeze drying and optionally injection moulding, the concentration of collagen in the solution prior to precipitation is preferably from 5 to 20 g/L, more preferably from 5 to 12 g/L, and most preferably from 9 to 10.5 g/L.

The total concentration of the one or more glycosaminoglycans in the solution prior to precipitation is typically from 0.01 to 1.5 g/L, more preferably from 0.01 to 1 g/L. Where the process includes the additional further steps of filtration and/or low temperature drying, the total concentration of the one or more glycosaminoglycans in the solution is more preferably from 0.03 to 1.25 g/L, still more preferably from 0.125 to 0.25 g/L, and most preferably from 0.13 to 0.182 g/L. Where the process includes the additional further steps of freeze drying and optionally injection moulding, the total concentration of the one or more glycosaminoglycans in the solution is more preferably from 0.15 to 1.5 g/L, still more preferably from 0.41 to 1.2 g/L, and most preferably from 0.78 to 0.96 g/L.

Preferably the solution comprises calcium ions and the ratio of collagen to the calcium ions is typically from 1:40 to 500:1 by weight. Where the process includes the additional further steps of filtration and/or low temperature drying, the ratio of collagen to the calcium ions is more preferably from 1:40 to 250:1, still more preferably 1:13 to 5:4, and most preferably 1:13 to 1:2. Where the process includes the additional further steps of freeze drying and optionally injection moulding, the ratio of collagen to the calcium ions is more preferably from 1:8 to 500:1, still more preferably 5:12 to 30:1, and most preferably 5:5 to 5:1.

Precipitation may be effected by combining the collagen, the calcium source, the phosphorous source and one or more glycosaminoglycans in an acidic aqueous solution and either allowing the solution to stand until precipitation occurs, agitating the solution, titration using basic titrants such as ammonia, addition of a nucleating agent such as pre-fabricated brushite, varying the rate of addition of the calcium source, and any combination of these techniques.

In a second aspect, the present invention provides a process for the production of a composite biomaterial comprising collagen, octacalcium phosphate and one or more glycosaminoglycans, said process comprising the steps of providing a composite material comprising collagen, brushite and one or more glycosaminoglycans, and converting at least some of the brushite in the composite material to octacalcium phosphate by hydrolysation.

The term biomaterial encompasses a material that is biocompatible with a human or animal body.

In the second aspect, the composite material preferably comprises or consists essentially of a triple co-precipitate comprising collagen, brushite and one or more glycosaminoglycans. The triple co-precipitate may be formed by a process as herein described in relation to the first aspect of the present invention.

Preferably, the step of hydrolysation (hydrolysis) of brushite to octacalcium phosphate comprises contacting the triple co-precipitate with an aqueous solution, said aqueous solution being at or above the pH at which octacalcium phosphate becomes thermodynamically more stable than brushite. Preferably, this aqueous solution has a pH of from 6 to 8. More preferably, this aqueous solution has a pH of from 6.3 to 7. Most preferably, this aqueous solution has pH of about 6.65. The aqueous solution may comprise, for example, deionised water whose pH is controlled with a titrant, a buffer solution, a solution saturated with respect to another calcium-containing compound and/or phosphorus-containing compound. A preferred aqueous solution comprises acetic acid titrated to the desired pH using ammonia.

Preferably, the step of hydrolysation of brushite to octacalcium phosphate is preformed at a temperature of from 20 to 50° C., more preferably from 30 to 40° C., still more preferably from 36 to 38° C., most preferably around 37° C.

Preferably, the step of hydrolysation of brushite to octacalcium phosphate is preformed for a time of from 12 to 144 hours, more preferably from 18 to 72 hours, most preferably from 24 to 48 hours.

In a third aspect, the present invention provides a process for the production of a composite biomaterial comprising collagen, apatite and one or more glycosaminoglycans, said process comprising the steps of providing a composite material comprising collagen, brushite and one or more glycosaminoglycans, and converting at least some of the brushite in the composite material to apatite by hydrolysation.

Apatite is a class of minerals comprising calcium and phosphate and has the general formula: $Ca_5(PO_4)_3(X)$, wherein X may be an ion that is typically $OH^-$, $F^-$ and $Cl^-$, as well as other ions known to those skilled in the art. Apatite also includes substituted apatites such as silicon-substituted apatites. Apatite includes hydroxyapatite, which is a specific example of an apatite. The hydroxyapatite may also be substituted with silicon.

In the third aspect, the composite material preferably comprises or consists essentially of a triple co-precipitate comprising collagen, brushite and one or more glycosaminoglycans. The triple co-precipitate may be formed according to the process as herein described in relation to the first aspect of the present invention.

Preferably, the step of hydrolysation (hydrolysis) of brushite to apatite comprises contacting the triple co-precipitate with an aqueous solution, said aqueous solution being at or above the pH at which apatite becomes thermodynamically more stable than brushite. Preferably, for the conversion of brushite to apatite, the aqueous solution has a pH of from 6.65 to 9, more preferably from 7 to 8.5, still more preferably from 7.2 to 8.5. The aqueous solution may comprise, for example, deionised water whose pH is controlled with a titrant, a buffer solution, a solution saturated with respect to another calcium-containing compound and/or phosphorus-containing compound.

Preferably, the step of hydrolysation of brushite to apatite is performed at a temperature of 20 to 50° C., more preferably from 30 to 40° C., still more preferably from 36 to 38° C., most preferably around 37° C.

Preferably, the step of hydrolysation of brushite to apatite is performed for a time of from 12 to 288 hours, more preferably from 18 to 72 hours, most preferably from 24 to 48 hours.

Methods of increasing the rate of conversion of brushite to octacalcium phosphate and/or apatite include (i) increasing the temperature, (ii) the brushite concentration in solution, and/or (iii) the agitation speed.

It may be desirable to produce a biomaterial according to the present invention comprising both apatite and octacalcium phosphate. The processes of the second and third aspects of the present invention may be combined to produce a material comprising both octacalcium phosphate and apatite. The brushite in the triple co-precipitate may first be converted to octacalcium phosphate and then the octacalcium phosphate may be partially converted to apatite. Total, or near total (i.e. at least 98%), conversion of brushite or octacalcium phosphate to apatite typically occurs by hydrolysation at a pH of 8.0 or more for a period of about 12 hours. Partial conversion of the brushite and/or apatite in the material may therefore be effected by hydrolysation for a period of less than 12 hours.

Preferably, the step of hydrolysation of octacalcium phosphate to apatite is carried out at a pH of from 6.65 to 10, more preferably from 7.2 to 10, still more preferably from 8 to 9.

Preferably, the step of hydrolysation of octacalcium phosphate to apatite is performed at a temperature of from 20 to 50° C., more preferably from 30 to 40° C., still more preferably from 36 to 38° C., most preferably around 37° C.

Preferably, the step of hydrolysation of octacalcium phosphate to apatite is performed for a time of from 2 to 144 hours, more preferably from 12 to 96 hours, most preferably from 24 to 72 hours.

In the second and third aspects of the present invention, the conversion of brushite to octacalcium phosphate and/or apatite is preferably conducted at a temperature of from 30 to 40 degrees centigrade. More preferably, the conversion is conducted at a temperature of from 36 to 38 degrees centigrade. Most preferably, the conversion is conducted at a temperature of about 37 degrees centigrade.

Preferably, the processes of the present invention further comprise the step of crosslinking the one or more glycosaminoglycans and the collagen in the triple co-precipitate. By triple co-precipitate this includes the triple co-precipitate comprising collagen, brushite and one or more glycosaminoglycans and derivatives of the co-precipitate. Derivatives include the co-precipitate wherein at least some of the brushite has been converted to octacalcium phosphate and/or apatite, and the co-precipitate that has been shaped or moulded, or subjected to any further chemical or mechanical processing. Crosslinking may be achieved using any of the conventional techniques.

Preferably, at least some of the brushite is converted to octacalcium phosphate and/or apatite, the glycosaminoglycan and collagen are crosslinked prior to the conversion of the brushite to octacalcium phosphate and/or apatite. This crosslinking may be effected by subjecting the triple co-precipitate to one or more of gamma radiation, ultraviolet radiation, a dehyrdothermal treatment, non-enzymatic glycation with a simple sugar such as glucose, mannose, ribose and sucrose, contacting the triple co-precipitate with one or more of glutaraldehyde, ethyl dimethylaminopropyl carbodiimide and/or nor-dihydroguariaretic acid, or any combination of these methods. These methods are conventional in the art.

Preferably, if at least some of the brushite is converted to octacalcium phosphate and/or apatite, the glycosaminoglycan and collagen are crosslinked subsequent to the conversion of the brushite to octacalcium phosphate and/or apatite. The crosslinking subsequent to the conversion of the brushite to apatite/octacalcium phosphate may be effected by one or more of the methods mentioned above or a dehydrothermal treatment, or any combination of these methods. A dehydrothermal treatment includes subjecting a substrate to a low pressure atmosphere at a raised temperature. The temperature in the dehydrothermal treatment may be of from 95° C. to 135° C. The temperature may preferably be of from 100° C. to 110° C., and most preferably of from 105° C. to 110° C., if completion of the dehydrothermal treatment is desired in typically 18 to 36 hours. The temperature may preferably be of from 120° C. to 135° C., and most preferably of from 125° C. to 135° C., if completion of the dehydrothermal treatment is desired in typically 4 to 8 hours.

Preferably, the collagen and the glycosaminoglycan are crosslinked both prior to and subsequent to conversion of the brushite to octacalcium phosphate and/or apatite.

The processes of the present invention may comprise the step of shaping the composite biomaterial into a structure suitable for use as a bone or dental substitute. Such a step may occur after formation of the triple co-precipitate, but prior to any conversion of the brushite or crosslinking of the collagen and glycosaminoglycan that may occur.

Alternatively, the step of shaping the biomaterial may occur subsequent to either the conversion of the brushite to apatite and/or octacalcium phosphate or crosslinking of the collagen and the glycosaminoglycan.

Preferably, the composite material is shaped using a technique selected from (i) filtration and/or low temperature drying, (ii) freeze drying, (iii) injection moulding and (iv) cold pressing. Filtration and/or low temperature drying, wherein the temperature is from 15° C. to 40° C., most preferably of from 35° C. to 40° C., typically results in a dense granular form of material. Freeze drying typically results in an open porous form. Injection moulding results in a wide variety of shapes/morphologies of a material depending on the shape of the dye used. Cold pressing typically results in a dense pellet form.

The present invention further provides a precursor material suitable for transforming into a synthetic biomaterial, said precursor material comprising a composite material comprising collagen, brushite and one or more glycosaminoglycans. Preferably, the composite material comprises or consists essentially of a triple co-precipitate comprising collagen, brushite and one or more glycosaminoglycans. The triple co-precipitate may be produced according to the process of the first aspect of the present invention.

The present invention also provides a composite biomaterial comprising collagen, brushite and one or more glycosaminoglycans, which biomaterial is obtainable by a process according to the present invention as herein described.

The present invention also provides a composite biomaterial comprising collagen, octacalcium phosphate and one or more glycosaminoglycans, which biomaterial is obtainable by a process according to the second aspect of the present invention.

The present invention also provides a composite biomaterial comprising collagen, apatite and one or more glycosaminoglycans, which biomaterial is obtainable by a process according to the third aspect of the present invention.

The present invention also provides a composite biomaterial comprising a triple co-precipitate of collagen, glycosaminoglycan and brushite.

The present invention also provides a biomaterial comprising particles of one or more calcium phosphate materials, collagen and one or more glycosaminoglycans, wherein said collagen and said one or more glycosaminoglycans are crosslinked and form a matrix, said particles of calcium phosphate material are dispersed in said matrix, and said calcium phosphate material is selected from one or more of brushite, octacalcium phosphate and/or apatite.

The following description relates to all aspects of the composite biomaterial according to the present invention unless otherwise stated.

The collagen and the one or more glycosaminoglycans have preferably been crosslinked.

The collagen is preferably present in the material in an amount of from 5 to 90 (dry) wt %, more preferably from 15 to 60 (dry) wt %, %, more preferably from 20 to 40 (dry) wt %.

Preferably, the one or more glycosaminoglycans are present in the material in an amount of from 0.01 to 12 (dry) wt %, more preferably from 1 to 5.5 (dry) wt %, most preferably from 1.8 to 2.3 (dry) wt %.

Preferably, if the material comprises brushite, the ratio of collagen to brushite is 10:1 to 1:100 by weight (dry), more preferably 5:1 to 1:20 by weight (dry), most preferably 3:2 to 1:10 by weight (dry), for example 3:2 to 1:4 by weight (dry).

Preferably if the material comprises octacalcium phosphate, the ratio of collagen to octacalcium phosphate is 10:1 to 1:100 by weight (dry), more preferably 5:1 to 1:20 by weight (dry), most preferably 3:2 to 1:10 by weight (dry).

Preferably, the ratio of collagen to the total amount of one or more glycosaminoglycans is from 8:1 to 30:1 by weight (dry), more preferably from 10:1 to 30:1 by weight (dry), still more preferably 10:1 to 12:1 by weight (dry), and most preferably 11:1 to 23:2 by weight (dry).

The composite biomaterial according to the present invention may be used as a substitute bone or dental material.

The present invention also provides a synthetic bone material, bone implant, bone graft, bone substitute, bone scaffold, filler, coating or cement comprising a composite biomaterial of the present invention. The term coating includes any coating comprising the biomaterial or precursor of the present invention. The coating may be applied to the external or internal surfaces of prosthetic members, bones, or any substrate intended for use in the human or animal body, which includes particulate materials. The composition of the present invention may be used for both in-vivo and ex-vivo repair of both mineralized biological material, including but not limited to bone and dental materials. The biomaterials of the present invention may be used in the growth of allografts and autografts.

The biomaterial according to the present invention comprising octacalcium phosphate may by free or essentially free of any of the precursor brushite phase. This biomaterial may comprise less than 2% by weight of brushite in total amount of calcium phosphate materials in the biomaterial.

The calcium phosphate material may comprise or consist essentially of phase pure octacalcium phosphate or apatite. By phase pure, this means preferably containing at least 98%, more preferably at least 99%, and most preferably, at least 99.5% of the desired phase (as measured by x-ray diffraction). Alternatively, the biomaterial may comprise a mixture of octacalcium phosphate and apatite, depending on the desired properties of the biomaterial.

The material of the present invention comprising brushite may be used either as a precursor material for making a biomaterial, or may be suitable in itself for use as a biomaterial.

The processes according to the present invention may be preformed using the following sequential method, which may be applied in whole or in part, to produce biocomposites of collagen, one or more glycosaminoglycan and one or more calcium phosphate constituents. The following description is provided by way of example and is applicable to any aspect of the processes according to the present invention.

I: Triple Co-precipitation of Collagen, GAG, and the Calcium Phosphate Brushite at Acidic pH This step is performed to initiate simultaneous formation, via precipitation from solution, of the three (or more) constituents of the composite, and to control the ratio of the three (or more) respective phases. Control of the compositional properties of the composite (and in particular the collagen: GAG:CaP ratio) may be achieved by varying one or more of the pH, temperature, ageing time, calcium ion concentration, phosphorous ion concentration, collagen concentration and GAG concentration. The pH may be maintained constant (using, for example, buffers, pH-stat titration or other methods) or be allowed to vary. The possible secondary (contaminant) phases include other acidic calcium phosphates (e.g. monetite, calcium hydrogen phosphate) and complexes including by-products of titration and reactant addition (e.g. ammonium phosphate, ammonium nitrate). Additives to aid crosslinking (e.g. glucose, ribose) or to enhance in-vivo response (e.g. growth factors, gene transcription factors, silicon, natriuretic peptides) may also be added during this step.

II: Net Shape Formation

This step may be performed to produce the desired architecture of the final composite form, with particular emphasis on control of pore architecture. Examples of techniques include filtration and low-temperature drying (resulting in a dense granular form), freeze drying (resulting in an open porous form), injection moulding (resulting in a wide range of shapes depending on the type of dye) and cold pressing (resulting in a dense pellet form).

III: Primary Crosslinking

This step may be performed to preferably ensure that, when placed in a solution of elevated pH, the GAG content of the composite does not elude rapidly, and, furthermore, to enhance the mechanical and degradation properties of the composite. Examples of techniques include low-temperature physical techniques (e.g. gamma irradiation, ultraviolet radiation, dehydrothermal treatment), chemical techniques (e.g. non-enzymatic glycation with a simple sugar, glutaraldehyde, ethyl dimethylaminopropyl carbodiimide, nordihydroguariaretic acid), or combination methods (e.g. simultaneous non-enzymatic glycation and gamma-irradiation). In the event that conversion to octacalcium phosphate (i.e. as in step IV) is desirable, primary crosslinking is advantageously performed at a temperature below about 37° C. to prevent conversion of the brushite phase to its dehydrated form, monetite, which is a calcium phosphate that does not readily hydrolyse to octacalcium phosphate.

IV: Hydrolysis

This step may be performed to partially or fully hydrolyse the CaP phase from brushite (phase with high solubility at physiological pH) to octacalcium phosphate and/or apatite (phases with lower solubility at physiological pH), and to substantially remove any soluble contaminant phases (e.g. ammonium nitrate, calcium hydrogen phosphate). In the case of hydrolysis to OCP, the selected pH is advantageously maintained constant at about 6.65 (using a buffer, pH stat, or other method), and the temperature at about 37° C. for around 24-48 hours. As was the case in Step I, additives to aid in crosslinking (e.g. glucose, ribose) or to enhance in-vivo response (e.g. growth factors, gene transcription factors, silicon, natriuretic peptides) may also be added during the hydrolysis step (Step IV).

V: Secondary Crosslinking

This step may be performed to further tailor the mechanical and degradation properties of the composite. Any or all of the crosslinking procedures listed in Step III above may be used to effect secondary crosslinking.

The following Examples and the accompanying Figures are provided to further assist in the understanding the present invention. The Examples and Figures are not to be considered limiting to the scope of the invention. Any feature described in the Examples or Figures is applicable to any aspect of the foregoing description.

EXAMPLE 1

Example 1 is an example of the synthesis method described above, executed via application of steps I through III only. Triple co-precipitation is carried out at room temperature (20-25° C.), at a pH of about 3.2 (maintained by titration with ammonia). In this example, co-precipitates are dried at 37° C. and crosslinked via a dehydrothermal treatment. Neither hydrolytic conversion of the CaP nor secondary crosslinking is performed in this example.

Materials

Collagen: Reconstituted, pepsin-extracted porcine dermal collagen (atelocollagen); 85% Type I, 15% Type III; Japan Meat Packers (Osaka, Japan)

GAG: Chondroitin-6-sulphate from shark cartilage; sodium salt; Sigma-Aldrich Inc (St. Louis, Mo., USA)

Calcium Sources: (i) Calcium hydroxide; $Ca(OH)_2$ Sigma-Aldrich Inc (St. Louis, Mo., USA), (ii) Calcium nitrate; $Ca(NO_3)_2 \cdot 4H_2O$; Sigma-Aldrich Inc (St. Louis, Mo., USA)

Phosphorous Source: Orthophosphoric acid; $H_3PO_4$; BDH Laboratory Supplies (Poole, United Kingdom)

Titrant: Ammonia; $NH_3$; BDH Laboratory Supplies (Poole, United Kingdom)

Procedure

Step I

Solution A:
Ca(OH)$_2$ is dissolved in 0.48 M H$_3$PO$_4$ to a concentration of 0.12 M at room temperature, and the resulting solution titrated to pH=3.2 using ammonia. Suspension B:
Chondroitin-6-sulphate is dissolved in dionised water to a concentration of 3.2 g/L. Under constant stirring, Ca(NO$_3$)$_2$.4H$_2$O and Ca(OH)$_2$ is then added to the chondroitin sulphate solution at a nitrate:hydroxide molar ratio of 1.5, to produce a suspension with a total calcium concentration of 2.4 M.
0.144 g collagen is added to 20 mL of Solution A, and blended using a homogeniser until dissolved. 4 mL of Suspension B is then added to Solution A under constant stirring.
Stirring is continued for 60 minutes, and pH monitored to ensure that it remains in the range 3.15<pH<3.30. The resulting slurry is then allowed to age for 24 hours at room temperature.

Step II

The slurry is allowed to dry at 37° C. in air for 5 days, and the remaining triple co-precipitate rinsed with deionised water, and subsequently dried again at 37° C. for an additional 24 hours.
The x-ray diffraction pattern of the resultant triple coprecipitate is shown in FIG. 1 (Cu—K(alpha) radiation) and an SEM image is shown in FIG. 2.

Step III

Triple co-precipitates are crosslinked via dehydrothermal treatment (DHT) at 105° C., under a vacuum of 50 mTorr, for 48 hours. A TEM image of the triple co-precipitate following DHT is shown in FIG. 3. FIG. 4 shows the x-ray diffraction pattern of the triple co-precipitate following DHT and indicates that the brushite phase has converted to its dehydrated form monetite.

EXAMPLE 2

Example 2 is an example of the synthesis method described above, executed via application of steps I through IV only. Triple co-precipitation is carried out at room temperature, and a pH of 4.0. In this example, pH control is effected by careful control of the calcium hydroxide and calcium nitrate concentrations—an approach that also enables control of the mass ratio of brushite to collagen plus GAG in the triple coprecipitate. The resulting triple co-precipitates are then frozen to −20° C., placed under vacuum and then heated to induce sublimation of unbound water (i.e. ice). Primary crosslinking is performed using a 1-ethyl 3-(3-dimethyl aminopropyl) carbodiimide treatment. The resulting dried triple coprecipitate is then converted to octacalcium phosphate via hydrolysis at a pH of 6.67 at about 37° C. In this example, secondary crosslinking is not performed.

Materials

Type I: Acid solubilised from bovine tendon Integra Life Sciences Plainsboro, N.J., USA
GAG: Chondroitin-6-sulphate from shark cartilage; sodium salt; Sigma-Aldrich Inc (St. Louis, Mo., USA)
Calcium Sources: (i) Calcium hydroxide; Ca(OH)$_2$ Sigma-Aldrich Inc (St. Louis, Mo., USA), and (ii) Calcium nitrate; Ca(NO$_3$)$_2$. 4H$_2$O; Sigma-Aldrich Inc (St. Louis, Mo., USA)
Phosphorous Source: Orthophosphoric acid; H$_3$PO$_4$; BDH Laboratory Supplies (Poole, United Kingdom)
Titrant: None
Crosslinking agents: (i) 1-Ethyl-3-(3-Dimethylaminopropyl) Carbodiimide (=EDAC); Sigma-Aldrich Inc (St. Louis, Mo., USA), and (ii) N-Hydroxysuccinimide (=NHS); Sigma-Aldrich Inc (St. Louis, Mo., USA)

Procedure

Step I

A target mass ratio of brushite to collagen plus glycosaminoglycan of 1:1 is selected.
The concentration of collagen plus GAG in a total reaction volume of 200 mL is set at 21 mg/mL.
Using an empirical, 3-dimensional map of pH variation (produced at a constant [Ca$^{2+}$] to [P] reactant ion ratio of 1.0) with differing (i) ionic concentrations (i.e. [Ca$^{2+}$]= [H$_3$PO$_4$]) and (ii) ratios of calcium nitrate:calcium hydroxide, a locus of points over which pH remained constant at 4.0 is identified. This is shown in FIG. 5 (sets of combinations of ionic concentration and calcium nitrate:calcium hydroxide ratio for maintaining pH=4.0).
Superimposing this locus of points onto a map of brushite mass yield with identical axes, and identification of its intersection with the 21 mg/mL contour allows the set of reactant concentrations for which a triple coprecipitate slurry containing a 1:1 mass ratio of calcium phosphate (21 mg/mL) to collagen plus GAG (21 mg/mL) can be produced at pH 4.0 ([Ca$^{2+}$]=[H$_3$PO$_4$]=0.1383 M; Ca(NO$_3$).4H$_2$O:Ca(OH)$_2$=0.1356) See FIG. 6: identification of conditions for pH 4.0 synthesis of a triple coprecipitate slurry containing a 1:1 mass ratio of calcium phosphate to collagen plus GAG.
3.8644 g collagen is dispersed in 171.4 mL of 0.1383 M H$_3$PO$_4$ cooled in an ice bath, by blending over 90 minutes at 15,000 rpm, using a homogeniser equipped with a stator 19 mm in diameter, to create a highly viscous collagen dispersion.
0.3436 g chondroitin-6-sulphate (GAG) is allowed to dissolve in 14.3 mL of 0.1383 M at room temperature, by shaking periodically to disperse dissolving GAG, producing a GAG solution.
After 90 minutes, the 14.3 mL of GAG solution is added to the mixing collagen dispersion at a rate of approximately 0.5 mL/min, under continuous homogenisation at 15,000 rpm, and the resulting highly-viscous collagen/GAG dispersion blended for a total of 90 minutes
After 90 minutes of mixing, 1.804 g Ca(OH)$_2$ and 0.780 g Ca(NO$_3$)$_2$.4H$_2$O are added to the highly-viscous collagen/GAG dispersion over 30 minutes under constant blending at 15,000 rpm, creating a collagen/GAG/CaP triple coprecipitate slurry, after which time an additional 14.3 mL of 0.1383 M H$_3$PO$_4$ is blended into the slurry
The pH of the triple coprecipitate slurry is approximately 4.0
The triple coprecipitate slurry is allowed to remain at 25° C. for a period of 48 hours.

Step II

The triple coprecipitate slurry is placed in a freezer at −20° C. and allowed to solidify overnight.
The frozen slurry is then removed from the freezer, placed in a vacuum of approximately 80 mTorr, and the temperature allowed to rise to room temperature, thus inducing sublimation of ice from the slurry, which is allowed to proceed over 48 hours.

The x-ray diffraction pattern of the collagen/GAG/brushite triple co-precipitate following removal of unbound water (Cu—K (alpha) radiation) is shown in FIG. 7, and an SEM image of the surface of a co-precipitate is shown in FIG. 8 (secondary (SE) and backscattered electron (BSE) images of surface of triple co-precipitate with CaP: collagen+GAG=1:1).

Step III

After complete removal of unbound water, 1.25 g of the resulting dry triple coprecipitate is hydrated in 40 mL deionised water for 20 minutes.

20 mL of a solution of 0.035 M EDAC and 0.014 M NHS is added to the container containing the triple coprecipitates and deionised water, and the triple coprecipitates allowed to crosslink for 2 hours at room temperature under gentle agitation.

The EDAC solution is removed, and the triple coprecipitates rinsed with phosphate buffer solution (PBS) and allowed to incubate at 37° C. for 2 hours in fresh PBS under mild agitation.

After two hours in PBS, the triple coprecipitates are rinsed with deionised water, and allowed to incubate for two 10-minute intervals at 37° C. under mild agitation.

The triple coprecipitates are then dried at 37° C. for 72 hours. FIG. 9 shows an x-ray diffraction pattern of the collagen/GAG/brushite triple coprecipitate following EDAC crosslinking (Cu—K (alpha) radiation).

Step IV

Crosslinked triple coprecipitate granules are placed in 50 mL deionised water at 37° C., and the pH of the solution adjusted to 6.67 using ammonia.

Temperature and pH are maintained constant for 48 hours, after which time the co-precipitates are filtered, rinsed in deionised water, and dried at 37° C. in air.

An x-ray diffraction pattern of the coprecipitates following conversion to OCP is shown in FIG. 10 (EDAC-crosslinked collagen/GAG/CaP triple co-precipitate following conversion at 37° C. to OCP over 72 hours at pH 6.67, to form a collagen/GAG/OCP biocomposite, Cu—K (alpha) radiation).

EXAMPLE 3

Example 3 is an example of the synthesis method described above, executed via application of steps I through V inclusive. Triple co-precipitation is carried out at room temperature, and a pH of about 4.5. As in example 2, pH control is effected by careful control of the calcium hydroxide and calcium nitrate concentrations, without the use of titrants. The resulting co-precipitates are then frozen to −20° C., placed under vacuum and then heated to induce sublimation of unbound water (i.e. ice). Primary crosslinking is performed using a 1-ethyl 3-(3-dimethyl aminopropyl) carbodiimide treatment. The resulting dried coprecipitate is then converted to apatite at pH 8.50, at 37° C. Secondary crosslinking performed using gamma irradiation.

Materials

Type I: Acid solubilised from bovine tendon Integra Life Sciences Plainsboro, N.J., USA GAG: Chondroitin-6-sulphate from shark cartilage; sodium salt; Sigma-Aldrich Inc (St. Louis, Mo., USA)

Calcium Sources: (i) Calcium hydroxide; $Ca(OH)_2$ Sigma-Aldrich Inc (St. Louis, Mo., USA), and (ii) Calcium nitrate; $Ca(NO_3)_2 \cdot 4H_2O$; Sigma-Aldrich Inc (St. Louis, Mo., USA)

Phosphorous Source: Orthophosphoric acid; $H_3PO_4$; BDH Laboratory Supplies (Poole, United Kingdom)

Titrant: None

Crosslinking agents: (i) 1-Ethyl-3-(3-Dimethylaminopropyl) Carbodiimide (=EDAC); Sigma-Aldrich Inc (St. Louis, Mo., USA) and (ii) N-Hydroxysuccinimide (=NHS); Sigma-Aldrich Inc (St. Louis, Mo., USA)

Procedure

Step I

A target mass ratio of brushite to collagen plus glycosaminoglycan of 3:1 is selected.

The concentration of collagen plus GAG in a total reaction volume of 200 mL is set at 10 mg/mL.

Using an empirical, 3-dimentional map of pH variation (at a constant $[Ca^{2+}]$ to [P] reactant ion ratio of 1.0) with differing i) ionic concentrations (i.e. $[Ca^{2+}]=[H_3PO_4]$) and ii) ratios of calcium nitrate: calcium hydroxide, a locus of points over which pH remained constant at 4.5 is identified. This is shown in FIG. 11 (set of combinations of ionic concentration and calcium nitrate: calcium hydroxide ratio for maintaining pH=4.5).

Superimposing this locus of points onto a map of brushite mass yield (with identical axes), and identification of its intersection with the 30 mg/mL (i.e. 3 times the concentration of collagen plus GAG) contour allows the set of reactant concentrations for which a triple coprecipitate slurry containing a 3:1 mass ratio of calcium phosphate (30 mg/mL) to collagen plus GAG (10 mg/mL) can be produced at a pH of 4.5 ($[Ca^{2+}]=[H_3PO_4]=0.1768$ M; $Ca(NO_3) \cdot 4H_2O:Ca(OH)_2=0.049$). This is show in FIG. 12: identification of conditions for pH 4.5 synthesis of a triple coprecipitate slurry containing a 3:1 mass ratio of calcium phosphate to collagen plus GAG.

1.837 g collagen is dispersed in 171.4 mL of 0.1768 M $H_3PO_4$ cooled in an ice bath, by blending over 90 minutes at 15,000 rpm, using a homogeniser equipped with a stator 19 mm in diameter, to create a collagen dispersion.

0.163 g chondroitin-6-sulphate (GAG) is allowed to dissolve in 14.3 mL of 0.1768 M at room temperature, by shaking periodically to disperse dissolving GAG, to produce a GAG solution.

After 90 minutes, the 14.3 mL of GAG solution is added to the mixing collagen dispersion at a rate of approximately 0.5 mL/min, under continuous homogenisation at 15,000 rpm, and the resulting collagen/GAG dispersion blended for a total of 90 minutes.

After 90 minutes of mixing, 2.498 g $Ca(OH)_2$ and 0.380 g $Ca(NO_3)_2 \cdot 4H_2O$ are added to the collagen/GAG dispersion over 30 minutes under constant blending at 15,000 rpm, creating a collagen/GAG/CaP triple coprecipitate slurry, after which time an additional 14.3 mL of 0.1768 M $H_3PO_4$ were added to the mixing slurry.

The pH of the triple coprecipitate slurry is approximately 4.5.

The triple coprecipitate slurry is allowed to remain at 25° C. for a period of 48 hours.

Step II

The triple coprecipitate slurry is placed in a freezer at −20° C. and allowed to freeze overnight.

The frozen slurry is then removed from the freezer, placed in a vacuum of approximately 80 mTorr, and the temperature allowed to rise to room temperature, thus inducing sublimation of the ice from the slurry, which is allowed to proceed over 48 hours. The x-ray diffraction trace of the collagen/GAG/brushite triple co-precipitate following removal of unbound water (Cu—K (alpha) radiation) is shown in FIG. 13.

Step III

After complete removal of unbound water, 1.25 g of the resulting dry triple coprecipitate is hydrated in 40 mL deionised water for 20 minutes.

20 mL of a solution of 0.018 M EDAC and 0.007 M NHS is added to the container containing the triple coprecipitates and deionised water, and the triple coprecipitates allowed to crosslink for 2 hours at room temperature, under gentle agitation.

The EDAC solution is removed, and the triple coprecipitates are rinsed with phosphate buffer solution (PBS) and allowed to incubate at 37° C. for 2 hours in fresh PBS under mild agitation.

After two hours in PBS, the triple coprecipitates are rinsed with deionised water, and allowed to incubate for two 10-minute intervals at 37° C. under mild agitation.

The triple coprecipitates are then dried at 37° C. for 72 hours. The x-ray diffraction pattern of collagen/GAG/brushite triple coprecipitate following EDAC crosslinking (Cu—K (alpha) radiation) is shown in FIG. 14.

Step IV

Crosslinked triple coprecipitate granules are placed in 50 mL deionised water pre-saturated with respect to brushite at 37° C., and the pH of the solution adjusted to 8.50 using ammonia.

The temperature and pH are maintained constant for 72 hours, after which time the co-precipitates are filtered, rinsed in deionised water, and dried at 37° C. in air. An x-ray diffraction pattern of the co-precipitates following conversion to apatite is shown in FIG. 15 (EDAC-crosslinked collagen/GAG/CaP triple co-precipitate following conversion at 37° C. to apatite over 72 hours at pH 8.50, to form a collagen/GAG/apatite biocomposite (Cu—K (alpha) radiation).

Step V

The dried collagen/GAG/Ap triple coprecipitates are subjected to a 32.1 kGy dose of gamma irradiation. FIG. 16 shows the x-ray diffraction pattern following gamma irradiation (EDAC-crosslinked collagen/GAG/Ap triple co-precipitates after secondary crosslinking via gamma irradiation).

EXAMPLE 4

Materials

Collagen: reconstituted, pepsin-extracted porcine dermal collagen (atelocollagen); 85% by weight of Type I, 15% by weight of Type III; Japan Meat Packers (Osaka, Japan)

GAG: Chondroitin-6-sulphate from shark cartilage; sodium salt; Sigma-Aldrich Inc (St. Louis, Mo., USA)

Calcium Sources: (i) Calcium hydroxide; $Ca(OH)_2$ Sigma-Aldrich Inc (St. Louis, Mo., USA), and (ii) Calcium nitrate; $Ca(NO_3)_2.4H_2O$; Sigma-Aldrich Inc (St. Louis, Mo., USA)

Phosphorous Source: Orthophosphoric acid; $H_3PO_4$; BDH Laboratory Supplies (Poole, United Kingdom)

Titrant: Ammonia; $NH_3$; BDH Laboratory Supplies (Poole, United Kingdom)

Procedure

Step I

Solution A was prepared by dissolving $Ca(OH)_2$ in 0.48 M $H_3PO_4$ to a concentration of 0.12 M at room temperature, and the resulting solution titrated to pH of 3.2.

Suspension B was prepared by dissolving Chondroitin-6-sulphate in deionised water to a concentration of 3.2 g/L. Under constant stirring, $Ca(NO_3)_2.4H_2O$ and $Ca(OH)_2$ then added to chondroitin sulphate solution at a nitrate:hydroxide molar ratio of 1.5, to produce a suspension with a total calcium concentration of 2.4 M.

0.144 g collagen were added to 20 mL of Solution A, and blended using a homogeniser until dissolved. 4 mL of Suspension B was then added to Solution A under constant stirring. Stirring was continued for 60 minutes, and pH monitored to ensure that it remained in the range $3.15 < pH < 3.30$. The resulting slurry was then allowed to age for 24 hours at room temperature.

Step II

The slurry was allowed to dry at 37° C. in air for 5 days, and the remaining triple co-precipitate rinsed with deionised water, and subsequently dried again at 37° C. for an additional 24 hours.

Step III

Co-precipitates were placed in dilute acetic acid (pH=3.2), and irradiated with a gamma irradiation dose of 30 kGy. The crosslinked precipitates were then removed from solution, rinsed, and dried at 37° C. in air.

Step IV

Crosslinked, co-precipitate granules were placed in 50 mL deionised water at 37° C., and the pH of the solution adjusted to 6.65 using ammonia. Temperature and pH were maintained constant for 48 hours, after which the co-precipitates were filtered, rinsed in deionised water, and dried at 37° C. in air.

Step V

Crosslinked, hydrolysed, co-precipitate granules were placed in a vacuum oven at room temperature, and a vacuum of 50 mTorr applied, after which the temperature was then increased to 105° C. After 24 hours, the temperature was reduced to room temperature and the vacuum released.

FIG. 17 shows the x-ray diffraction pattern of the composite immediately following triple co-precipitation and drying (Steps I and II). This pattern confirms the major phase present to be brushite.

Figure 18:
FIG. 18: SEM micrograph of the structure of co-precipitate granules following primary cross-linking of Example 4.

FIG. 18 shows an SEM micrograph of the structure of co-precipitate granules following primary crosslinking (Step III). It is worthy to note the microstructurally homogeneous nature of the granules.

Figure 19:
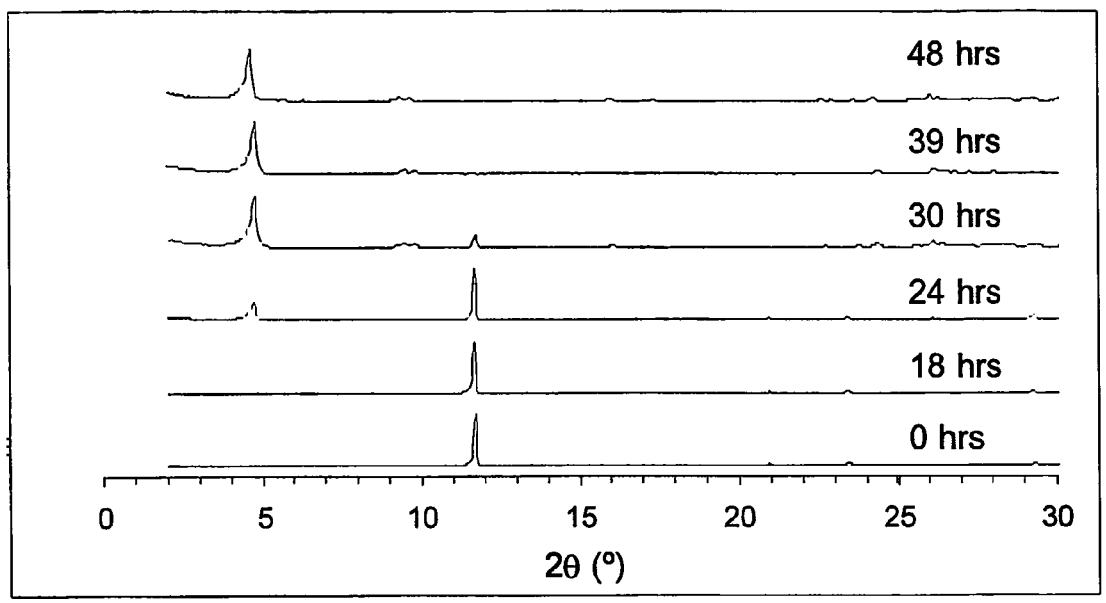
FIG. 19: XRD pattern illustrating the progression of hydrolysis to octacalcium phosphate in Example 4.

The progression of hydrolysis to octacalcium phosphate (Step IV) is illustrated in the XRD Pattern of FIG. 19. Progressive decreases in the intensity of the brushite peak at 12.5°, and increases of the major octacalcium phosphate (OCP) peak at 4.5° indicate the conversion of the inorganic phase to OCP over a period of 48 hours.

Figure 20:
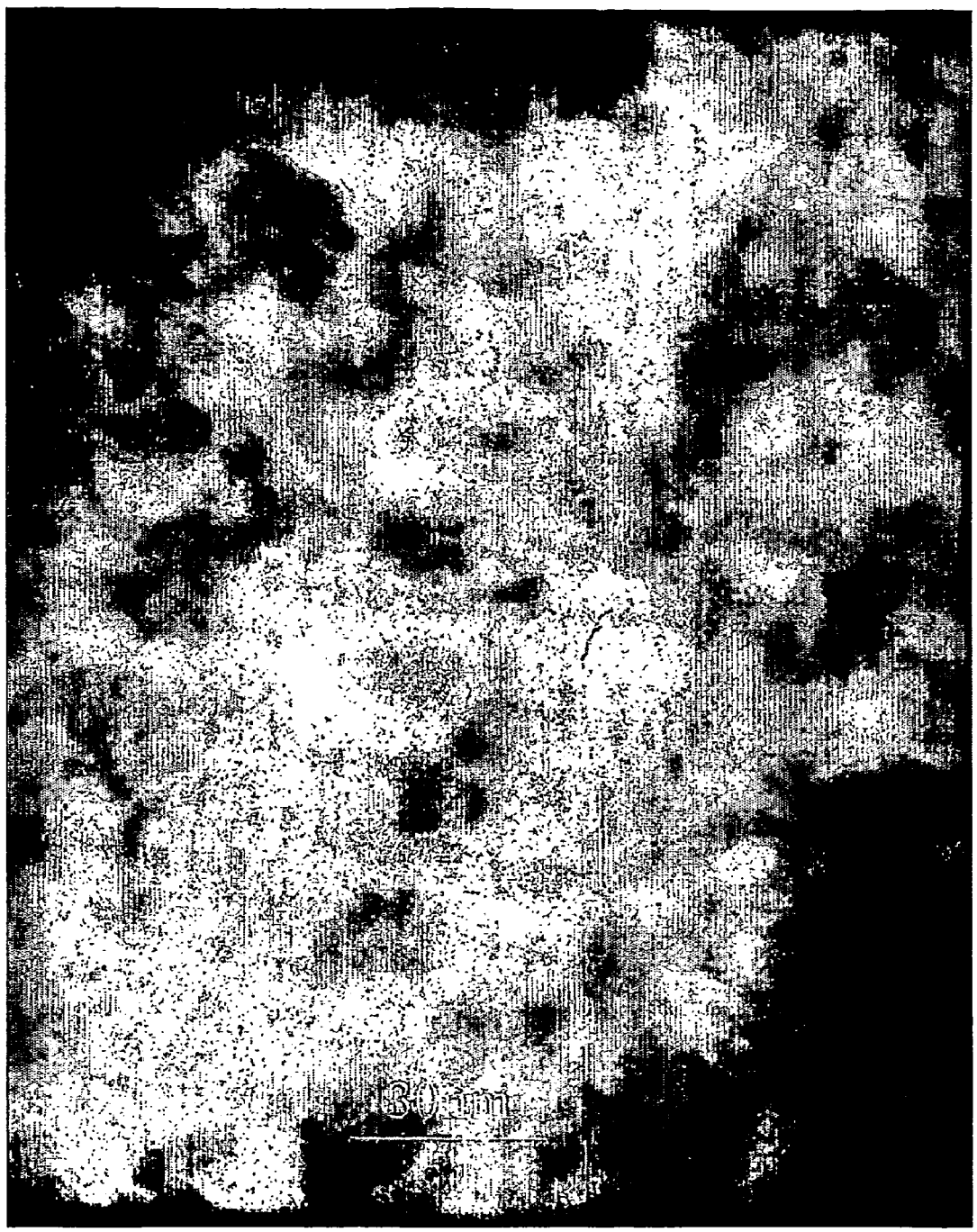
FIG. 20: TEM image of a composite of Example 4.

A TEM image of the composite is shown in FIG. 20. A random distribution of 10-20 nm low aspect-ratio calcium phosphate crystals dispersed in a collagen/GAG matrix is evident.

The composite biomaterials of the present invention may be used as a bioresorbable material. Following implantation, it is expected that a device fabricated from the material would resorb completely, leaving behind only healthy, regenerated tissue, with no remaining trace of the implant itself.

The invention claimed is:

1. A process for the production of a composite material comprising collagen, brushite and one or more glycosaminoglycans, said process comprising the steps of
providing an acidic aqueous solution comprising collagen, a calcium source and a phosphorous source and one or more glycosaminoglycans, and
precipitating the collagen, the brushite and the one or more glycosaminoglycans together from the aqueous solution to form a triple co-precipitate.

2. The process as claimed in claim 1, wherein the solution has a pH of from 2.5 to 6.5.

3. The process as claimed in claim 1, wherein the calcium source is selected from one or more of calcium nitrate, calcium acetate, calcium chloride, calcium carbonate and calcium alkoxide, calcium hydroxide, calcium silicate, calcium sulphate, calcium gluconate and the calcium salt of heparin.

4. The process as claimed in claim 1, wherein the phosphorus source is selected from one or more of ammonium-dihydrogen phosphate, diammonium hydrogen phosphate, phosphoric acid, disodium hydrogen orthophosphate 2-hydrate and trimethyl phosphate.

5. The process as claimed in claim 1, wherein the one or more glycosaminoglycans are selected from chondroitin sulphate, dermatin sulphate, heparin, heparin sulphate, keratin sulphate and hyaluronic acid.

6. The process as claimed in claim 1, wherein the solution has a temperature of from 4 to 50° C.

7. The process as claimed in claim 1, wherein the ratio of collagen to the total amount of one or more glycosaminoglycans in the solution is from 8:1 to 30:1 by weight.

8. The process as claimed in claim 1, wherein the solution comprises calcium ions and the ratio of collagen to the calcium ions is from 1:40 to 500:1 by weight.

9. The process as claimed in claim 1, wherein the ratio of collagen to brushite in the co-precipitate is from 10:1 to 1:100 by weight.

10. The process as claimed in claim 1, wherein the solution comprises calcium ions and the concentration of calcium ions in solution is from 0.00025 to 1 M.

11. The process as claimed in claim 1, wherein the solution comprises phosphate ions and the concentration of phosphate ions in the solution is from 0.00025 to 1 M.

12. The process as claimed in claim 1, wherein the concentration of collagen in the solution is from 1.0 to 20 g/L.

13. The process as claimed in claim 1, wherein the total concentration of the one or more glycosaminoglycans in the solution is from 0.01 to 1.5 g/L.

14. The process as claimed in claim 1, further comprising the steps of crosslinking the collagen and the one or more glycosaminoglycans in the triple co-precipitate.

15. The process of claim 1 wherein the aqueous solution is a solution/dispersion.

16. The process as claimed in claim 2, wherein the solution has a pH of from 3 to 4.5.

17. The process as claimed in claim 16, wherein the solution has a pH of from 3.8 to 4.2.

18. A process for the production of a composite biomaterial comprising collagen, octacalcium phosphate and one or more glycosaminoglycans, said process comprising the steps of
providing a composite material comprising a triple co-precipitate of collagen, brushite and one or more glycosaminoglycans, and
converting at least some of the brushite in the composite material to octacalcium phosphate by hydrolysation.

19. The process as claimed in claim 18, wherein the composite material consists essentially of the triple co-precipitate comprising collagen, brushite and one or more glycosaminoglycans.

20. The process as claimed in claim 18, wherein the step of hydrolysation of brushite to octacalcium phosphate comprises contacting the composite material with an aqueous solution, said aqueous solution being at or above the pH at which octacalcium phosphate becomes thermodynamically more stable than brushite.

21. The process as claimed in claim 20, wherein said aqueous solution has a pH of from 6 to 8.

22. The process as claimed in claim 21, wherein said aqueous solution has a pH of from 6.3 to 7.

23. A process for the production of a composite biomaterial comprising collagen, apatite and one or more glycosaminoglycans, said process comprising the steps of
providing a composite material comprising a triple co-precipitate of collagen, brushite and one or more glycosaminoglycans, and
converting at least some of the brushite in the composite material to apatite by hydrolysation.

24. The process as claimed in claim 23, wherein the conversion of brushite to apatite is carried out at a temperature of from 20 to 50° C.

25. The process as claimed in claim 23, wherein the composite material consists essentially of the triple co-precipitate comprising collagen, brushite and one or more glycosaminoglycans.

26. The process as claimed in claim 23, wherein the step of hydrolysation of brushite to apatite comprises contacting the composite material with an aqueous solution, said aqueous solution being at or above the pH at which apatite becomes thermodynamically more stable than brushite.

27. The process as claimed in claim 26, wherein said aqueous solution has a pH of from 6.65 to 9.

28. A precursor material for transforming into a synthetic biomaterial, said precursor material comprising a composite material comprising collagen, brushite and one or more glycosaminoglycans wherein the composite material comprises a triple co-precipitate comprising the collagen, the brushite and the one or more glycosaminoglycans.

29. The precursor material as claimed in claim 28, wherein the composite material consists essentially of the triple co-precipitate comprising the collagen, the brushite and the one or more glycosaminoglycans.

30. A composite biomaterial comprising a triple co-precipitate of collagen, brushite and one or more glycosaminoglycans.

31. A biomaterial comprising triple co-precipitate particles of one or more calcium phosphate materials, collagen and one or more glycosaminoglycans, wherein said collagen and said one or more glycosaminoglycans are crosslinked and form a matrix,
said particles of calcium phosphate material are dispersed in said matrix, and
said calcium phosphate material is selected from one or more of brushite, octacalcium phosphate and/or apatite.

* * * * *